US 008744876B2

(12) United States Patent
Gross

(10) Patent No.: US 8,744,876 B2
(45) Date of Patent: Jun. 3, 2014

(54) METHOD AND SYSTEM FOR PROVIDING A PATIENT IDENTIFICATION BEACON FOR PATIENT WORN SENSORS

(75) Inventor: Brian Gross, North Andover, MA (US)

(73) Assignee: Koninklijke Philips N.V., Eindhoven (NL)

(*) Notice: Subject to any disclaimer, the term of this patent is extended or adjusted under 35 U.S.C. 154(b) by 179 days.

(21) Appl. No.: 13/055,179

(22) PCT Filed: Aug. 11, 2009

(86) PCT No.: PCT/IB2009/053548
§ 371 (c)(1),
(2), (4) Date: Jan. 21, 2011

(87) PCT Pub. No.: WO2010/023577
PCT Pub. Date: Mar. 4, 2010

(65) Prior Publication Data
US 2011/0125535 A1    May 26, 2011

Related U.S. Application Data

(60) Provisional application No. 61/092,455, filed on Aug. 28, 2008.

(51) Int. Cl.
*G06Q 50/00* (2012.01)
(52) U.S. Cl.
USPC .................................. 705/3; 705/2; 600/300
(58) Field of Classification Search
CPC ...... G06Q 50/22; G06Q 50/24; G06F 19/322; G06F 19/3418; G06F 19/327; G06F 19/345; G06F 19/323

USPC ........................................ 705/2–3; 600/300
See application file for complete search history.

(56) References Cited

U.S. PATENT DOCUMENTS

| 5,572,401 A | 11/1996 | Carroll |
| 2002/0165733 A1* | 11/2002 | Pulkkinen et al. ................ 705/2 |
| 2003/0016122 A1* | 1/2003 | Petrick ....................... 340/10.41 |

(Continued)

FOREIGN PATENT DOCUMENTS

| RU | 2286600 C1 | 10/2006 |
| WO | 2006035351 A2 | 4/2006 |

(Continued)

OTHER PUBLICATIONS

Chowdhury, B., et al.; RFID-based Hospital Real-time Patient Management System; 2007; Computer and Information Science; ICIS 2007; pp. 363-368.

*Primary Examiner* — Sind Phongsvirajati

(57) ABSTRACT

A bracelet beacon device (10) includes a flexible material strap (16) which encases or is attached to a writable layer (22) carrying human readable patient identification information, a flexible power supply (26), and a flexible circuit layer (24). The flexible circuit layer includes a memory (40) for storing at least patient identification information and a body coupled communication transmitter (42) for transmitting the patient identification information via the patient using a body coupled communication protocol.

15 Claims, 4 Drawing Sheets

(56) References Cited

U.S. PATENT DOCUMENTS

| | | | |
|---|---|---|---|
| 2003/0140929 A1* | 7/2003 | Wilkes et al. | 128/898 |
| 2003/0144878 A1* | 7/2003 | Wilkes et al. | 705/2 |
| 2004/0193453 A1* | 9/2004 | Butterfield et al. | 705/2 |
| 2005/0055244 A1* | 3/2005 | Mullan et al. | 705/2 |
| 2005/0065817 A1* | 3/2005 | Mihai et al. | 705/2 |
| 2006/0004606 A1* | 1/2006 | Wendl et al. | 705/2 |
| 2007/0132597 A1* | 6/2007 | Rodgers | 340/573.1 |
| 2007/0136103 A1 | 6/2007 | Kim et al. | |
| 2008/0300055 A1* | 12/2008 | Lutnick et al. | 463/39 |

FOREIGN PATENT DOCUMENTS

| | | |
|---|---|---|
| WO | 2006051464 A1 | 5/2006 |
| WO | 2007012998 A1 | 2/2007 |
| WO | 2007041843 A1 | 4/2007 |
| WO | 2007084807 A1 | 7/2007 |

* cited by examiner

METHOD AND SYSTEM FOR PROVIDING A PATIENT IDENTIFICATION BEACON FOR PATIENT WORN SENSORS

CROSS REFERENCE TO RELATED APPLICATIONS

This application claims the benefit of U.S. provisional application Ser. No. 61/092,455 filed Aug. 28, 2008, which is incorporated herein by reference.

The present application relates to the medical arts. It finds particular application in conjunction with patient identification, physiologic data collection, and treatment, and will be described with particular reference thereto. However, it is to be appreciated that it will find other applications such as identifying medical professionals and other people, patient-caregiver interactions, other interactions, security, and the like.

Today, there is an enormous challenge matching data from the multitude of data generating monitoring devices, to the correct patient identification. Typically when entering a medical facility, a typed or printed patient ID is affixed to the patient's wrist or ankle with a bracelet. Such bracelets typically utilize a printed label sealed into a transparent strip that is affixed around the wrist or ankle. Nurses, doctors, surgeons, and other caregivers refer to this bracelet to verify patient identity. When tests are performed, physiological parameters read, and the like, the caregiver associates the test results, readings, and the like with the patient ID in a hospital database system. Such a manual procedure is subject to human error.

Others have proposed barcoding the patient ID onto the bracelet. A barcode reader then scans the bracelet to determine the patient ID. Although automated barcode reading reduces errors, the process is still primarily a manual process.

Others have proposed electronic monitoring device which transmit monitored information with the patient ID to the central database system. Because sending data with the patient's ID violates patient confidentiality, complex encrypting schemes were needed.

The present application provides a new and improved apparatus and system which overcomes the above-referenced problems and others.

In accordance with one aspect, a beacon apparatus includes a strap of flexible material configured to be attached to an extremity of a patient, a printable layer attached to the strap, a flexible power supply attached to the strap, and a flexible circuit attached to the strap and the power supply. The flexible circuit includes a wireless transmitting unit which wirelessly transmits at least patient identification information.

In accordance with another aspect, a hospital system includes a plurality of the beacon apparatuses for attachment to a plurality of patients. A beacon containing a unique ID is associated with a specific patient in the master patient index (typically done at the time the beacon is applied to the patient). The beacon ID can represent the patient and all data which is received from or transmitted to other beacon apparatuses. A diagnostic or testing apparatus receives patient information and provides diagnostic or test information associated with the beacon identification information to the medical facility. A medical facility system identifies the patient associated with the beacon ID, stores and retrieves patient information with the identified patient. A display end user input device is connected with the transceiver.

In accordance with another aspect, a method of associating information with a patient includes printing human-readable patient information on a printable layer, attaching the printable layer, a strap of flexible material, a flexible circuit layer, and a power supply together. The flexible strap with the attached printable layer, flexible circuit layer, and flexible power supply is attached to an extremity of a patient. At least patient identification information is wirelessly transmitted from the flexible circuit layer.

One advantage resides in a reducing of human error in patient records.

Another advantage resides in reduced labor to maintain patient records.

Another advantage resides in improved patient treatment.

Still further advantages of the present invention will be appreciated by those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
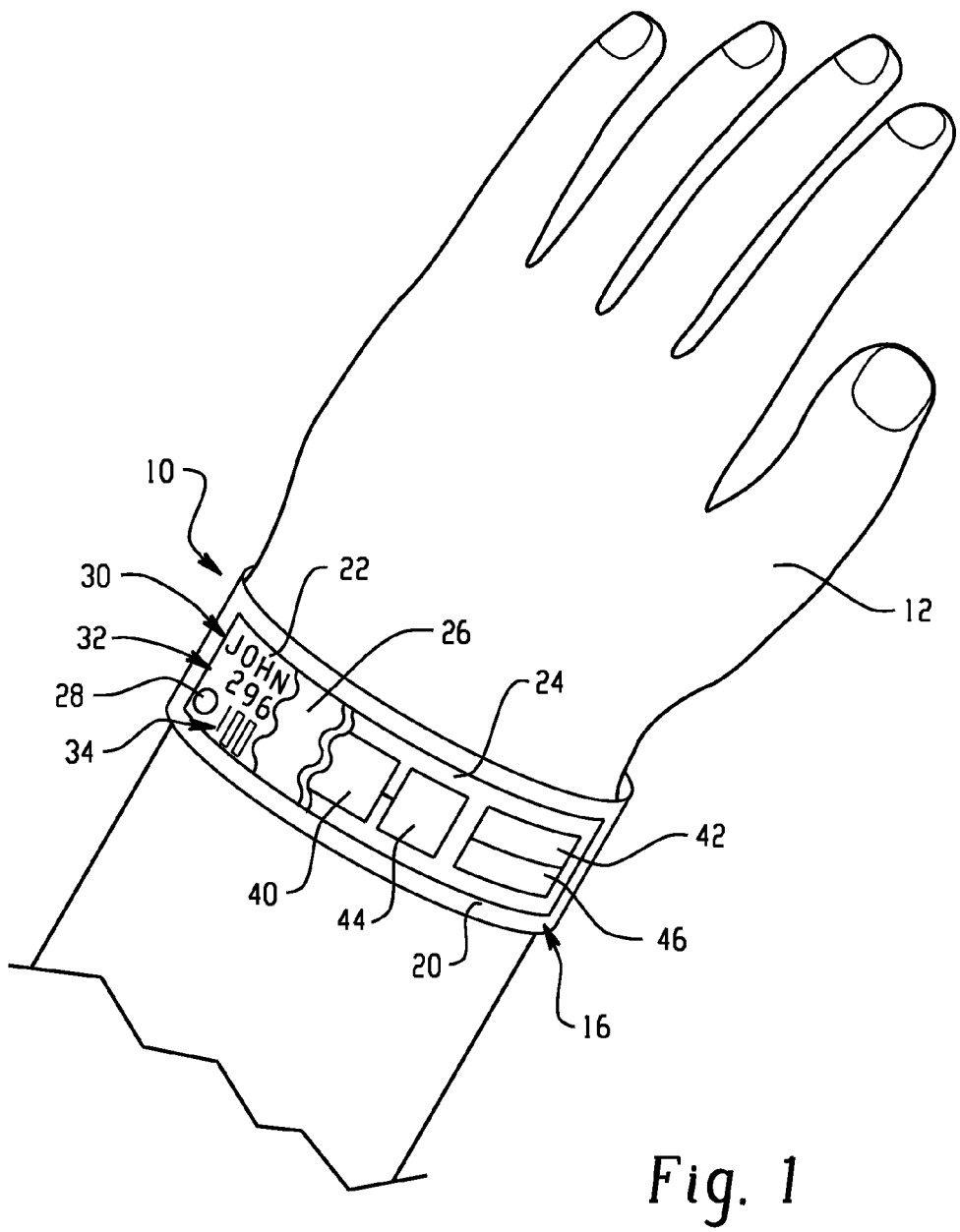
FIG. 1 is a diagrammatic illustration of a bracelet beacon device in partial section worn around a patient's wrist.

With reference to FIG. 1, a beacon in the form of a disposable bracelet 10 is attached to a patient for a length of stay in a medical facility. The bracelet device 10 is often worn around a wrist 12 of a patient 14 as an arm bracelet. However, the beacon may be attached to the patient in other locations including, but not limited to the wrist, the upper arm, the ankle, above the knee, around the neck as a collar or necklace, around the waist, or the like.

The beacon bracelet device 10 includes a strap 16 which, in one embodiment, is a light-weight, flexible material, such as plastic, mylar, treated paper, bacteriostatic material, and the like. In one embodiment, the strap 16 is in the form of a transparent plastic tube into which relatively flat structures can be inserted from the end. The bracelet includes a fastening construction that enables the bracelet device to be fitted around the patient's extremity. In some embodiments, the fastening construction prohibits the beacon bracelet device from being removed without at least partial destruction. In accordance with one aspect, the removal of the beacon from the patient causes the beacon to signal that the beacon was removed to alert the receiving data systems to the potential that the beacon is no longer associated. Typically, the beacon bracelet device 10 is removed and disabled when a patient is discharged.

In the illustrated embodiment, the beacon bracelet device 10 includes a transparent plastic strip 20 in the form of an elongated tube or which is foldable to define an interior space for receiving relatively flat constructions. A printable layer 22, such as a paper strip, a thin flexible circuit layer 24, and a power supply 26, preferably a thin, flexible battery, are inserted or sealed into the plastic strip 20. The power supply 26 can include a single use battery that is activated when the bracelet device is installed on a patient, rechargeable batteries or capacitors, and the like. A battery charge indicator 28, e.g., a color indicator, is connected with the flexible circuit layer and positioned to be viewable from the exterior of the bracelet device.

The printable layer 22 typically includes a patient's name and basic demographics 30 in human readable form, a hospital identification number 32 in human-readable form, and a machine-readable patient identifiers 34 such as a bar code. Other relevant information such as admission date, emergency physiological information such as blood type or allergies, purpose of admission to the medical facility, attending physician, and the like can also appear on the printable layer 22.

The flexible circuit layer includes a memory 40 that stores at least a unique beacon identification or ID. At initial intake, the patient or the patient ID is associated with the beacon ID such that a medical facility data system can associate received data with the correct system. Alternately, the patient ID 32 can be stored in the beacon memory as the beacon ID, provided that transmitted data is encrypted. The memory 40 can also store patient monitor readings such as blood pressure, SpO2, pulse rate, ECG, etc., medication administration record, clinical laboratory values known for the patient, date and time of significant events, encryption key(s), attending physician identification, medical history, other medical information, processor control programs or information, and the like. A transmitter 42 transmits the patient ID which is stored in the memory 40 and other information with a lower power protocol, such as body coupled communications (BCC). A processor 44 controls the transmitter to send the patient identification information, e.g., periodically to increase battery life, on demand, or the like. Typical periods might be once a minute for a patient beacon, once every five seconds for a clinical beacon, once an hour for an infrastructure beacon, once every 15 seconds for pumps and monitors. Beaconing can also by triggered manually, in response to an event such as an IV being connected, etc. The flexible circuit may include a manually actuatable switch for manually causing the patient ID to be transmitted. A receiver 46 receives information using the low power protocol and communicates the received information to the processor. The received information can include a request to transmit the patient ID, data to be recorded in the memory 40, instructions to retrieve and transmit data from the memory, and the like.

Figure 2:
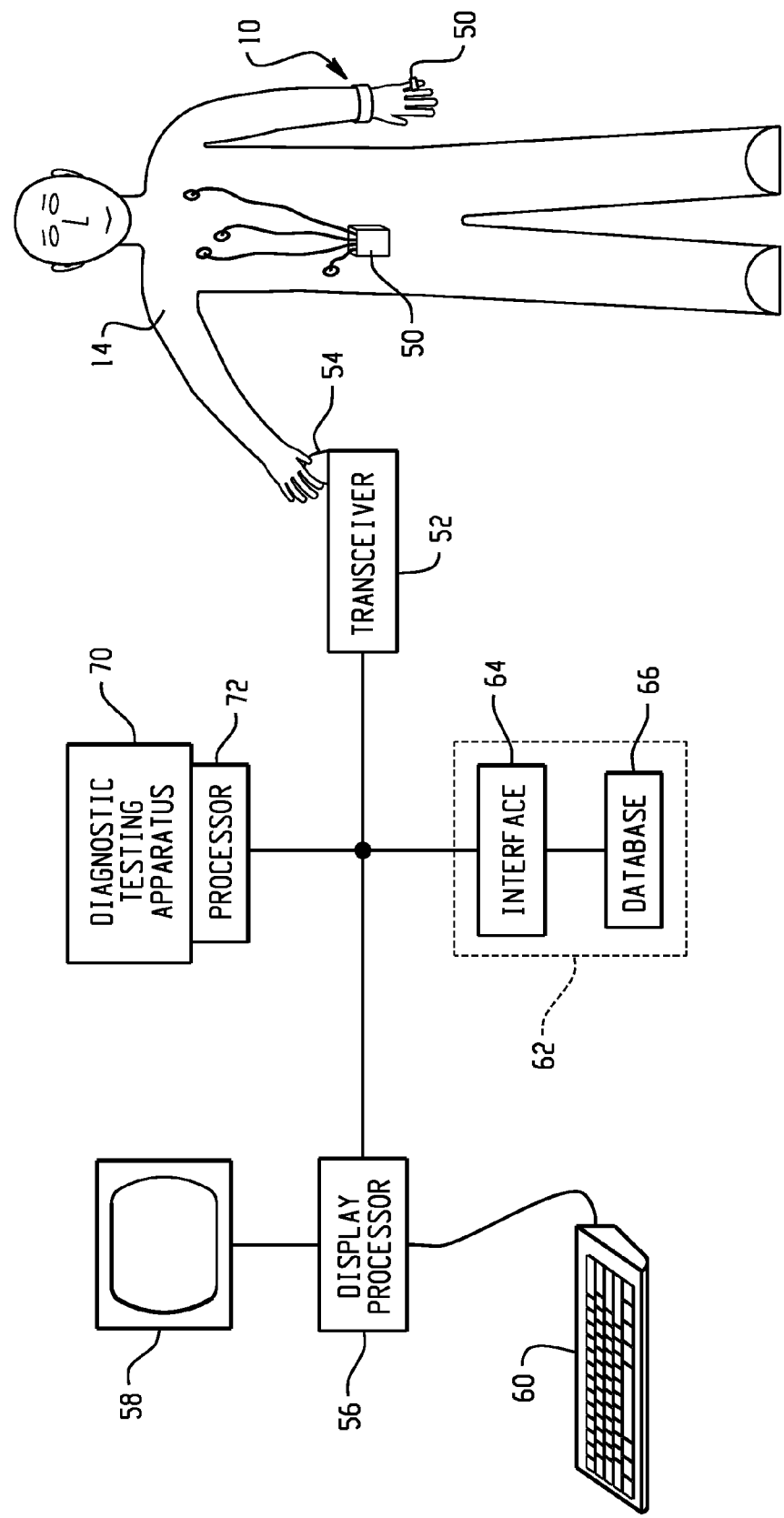
FIG. 2 is a diagrammatic illustration of a patient outfitted with the bracelet beacon device and a system for exchanging information with the bracelet beacon device.

With reference to FIG. 2, the beacon bracelet device 10 uses the body coupled communications protocol to poll or otherwise access patient worn physiological parameter sensors 50 such as an SpO2 monitor, a pulse monitor, an ECG monitor, or the like which are equipped with appropriate electronics to transmit and receive body coupled communications. By touching an associated medical device with body coupled communications capabilities, such as an IV pump, syringe, and the like, information about medications given to the patient can be downloaded to the beacon for transmission to the medical facility system. Also, information about blood type, medicinal allergies, and the like communicated to the associated device or another warning device. Preferably, the processor 44 of the beacon device exchanges encryption keys with the sensors 50 such that the communicated physiological data is encrypted.

The patient ID and other information from the beacon can be transmitted to a transceiver 52 when the patient touches or comes in close proximity to a body coupled communications sensor plate or antenna 54 which can be shaped to accommodate the human hand. The transceiver is connected with one or more of a variety of systems which receive information from or transmit information to the beacon. For example, the transceiver can be connected with a display controller or processor 56, which controls a human readable monitor 58 to display the patient ID, monitored physiological data, warnings, or other information. A user interface 60, such as a keyboard or mouse, enables a human operator to input information to the transceiver to be transferred to the beacon. The user interface may be used in initially programming the patient ID and other information into the memory 40 when the bracelet device 10 is first attached to the patient.

The transceiver is also connected to a hospital or other medical system 62 including an interface 64 and a database 66. The interface includes or accesses a look-up table or memory which correlates the unique beacon ID (if different from the patient ID) with the corresponding patient. During initial intake or when the beacon is attached to a patient, the correlation between the patient and the beacon ID are loaded into the look-up table or memory, e.g., by the transceiver 52 and the user interface 60. Information from the memory 40 can be transferred via the transceiver 52 and interface 64 to the hospital system database 66 to become part of the patient record. Conversely, other patient information and the beacon ID associated with the patient can be read out of the hospital database and transferred by the transceiver 52 to the memory 40 to transfer the other patient information to the beacon. In the encryption embodiment in which the beacon ID is the same as the patient ID, the patient ID is also transferred by the transceiver to the memory 40.

The transceiver 52, in another embodiment, is connected to a diagnostic or testing apparatus 70. Various diagnostic or testing apparatus are contemplated, such as blood pressure cuff, a blood analysis machine, a diagnostic imaging apparatus, a blood or other specimen collection machine, and the like. The apparatus 70 includes a processor or interface 72 which receives the patient ID from the transceiver 52 and associates the ID of the patient touching or in close proximity to the plate 54 with diagnostic or test results, collected specimens, or the like.

Figure 3:
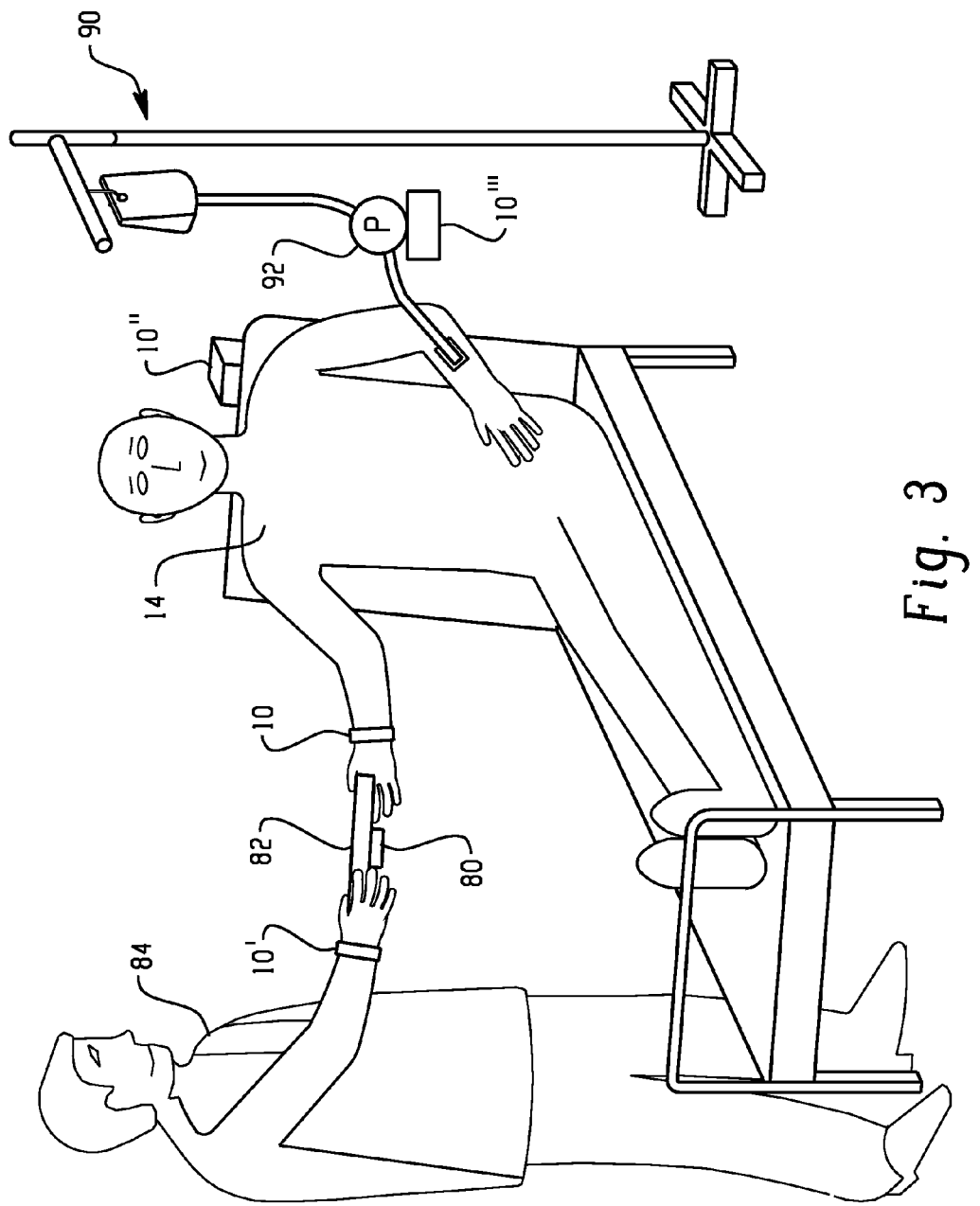
FIG. 3 is a diagrammatic illustration illustrating interaction between a patient equipped with the bracelet beacon device and a medical appliance or caregiver carrying a body coupled communication device; and, FIG. 4 is a flowchart illustrative of a method of using the system of FIGS. 1-3.

With reference to FIG. 3, a body coupled communication unit 80 can be connected with various peripherals such as a pill tray 82. When the body coupled communication device 80 is programmed with the pills or other medications in the pill tray, that information is transferred to the beacon 10 via body coupled communications when the patient 14 touches or picks up the pill tray. Other peripherals, such as specimen bottles, and the like, can also include a body coupled communication device. For a specimen bottle, the patient ID from the beacon 10 is transmitted via body coupled communications to the body coupled communication device on the specimen bottle in order to assure that the patient ID and the specimen stay together. In this embodiment, the sample collection container with a beacon is capable of capturing both the patient ID from the beacon on the patient and the one worn by the clinician acquiring the patient's blood sample, as well as time of acquisition automatically. Then later this data and information is communicated to the clinical analyzer so the acquisition details are obtained, and results are reported to the correct patient's record automatically and error free.

Similarly, a caregiver 84 can wear an analogous beacon 10' which may be in the form of a bracelet and may have substantially identical structure to the bracelet device 10 worn by the patient 14. Alternately, the care giver beacon may be of a slightly different structure in order to facilitate removal on leaving the hospital after a shift, recharging a battery, or the like. Whenever the caregiver touches the patient directly or via a peripheral, body coupled communication is established between the beacons 10, 10'. In this manner, the patient or the caregiver can record patient interactions and personally administered treatments. For example, if the caregiver uses a stethoscope to monitor the patient's heart, the stethoscope provides a body coupled communication channel between the patient and caregiver, enabling the caregiver and the time of the treatment or interaction to be recorded. When the patient or caregiver touches the plate 54 of the transceiver 52 of the medical facility system, this information can be downloaded into the medical facility system 62.

In one embodiment, the patient bed is connected with a patient bed beacon 10″. In another embodiment, a transceiver 52′ is mounted on the bed. The bed beacon 10″ or bed transceiver 52′ communicates with the beacon 10 using body coupled communications protocol via the bed. The bed beacon or transceiver can have a large or rechargeable battery or can be connected to a remote power supply. The bed beacon or transceiver can communicate with the medical facility system 62 wirelessly, by a wired connection, or a combination thereof.

In another embodiment, an IV 90 is disposed adjacent the patient. An IV pump 52 includes an IV beacon 10‴ which communicates medical dosage information to the patient beacon 10 using a body coupled communication protocol. The IV fluids provide a body coupled communications path.

Figure 4:
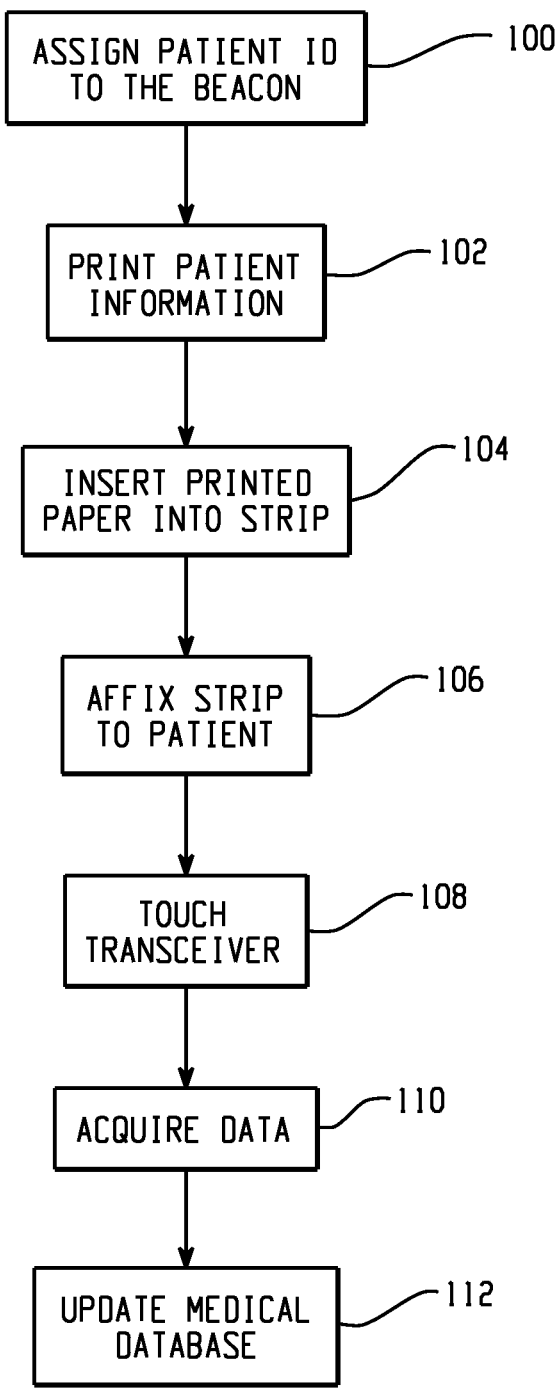

With reference to FIG. 4, in use, the beacon, particularly the memory 40 of the bracelet device 10, is assigned 100 a patient ID code. Alternately, if the memory 40 is preprogrammed with a bracelet ID, that bracelet ID is associated with a patient ID in the hospital system. Patient information is printed 102 on the printable layer 22, and the printable layer is inserted or affixed 104 into the strap 16 which has previously received the battery and circuit layers. The strap 16 is wrapped around the wrist or other patient extremity and affixed 106 to the patient. The patient touches 108 the transceiver 52 to establish BCC communication with the hospital system to upload appropriate patient ID and medical information to the memory 40.

The beacon acquires data from the physiological monitors 50, from interaction with peripherals 82, from interaction with a caregiver, from interaction with a diagnostic or testing apparatus 70, or the like. Periodically, the patient 14 touches or comes sufficiently close to the transceiver 52 that the hospital database 66 is updated 112.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A beacon system comprising:
   a strap of flexible material configured to be attached to an extremity of a patient;
   a printable layer attached to the strap;
   a flexible power supply attached to the strap; and,
   a flexible circuit attached to the strap and the power supply, the flexible circuit including:
   a memory configured to store at least beacon or patient identification information,
   a wireless transmitting unit configured to wirelessly transmit, via body coupled communication, at least the beacon or patient identification information,
   a receiving unit configured to receive encrypted information, and
   a processor configured to communicate at least the beacon or patient identification information from the memory to the transmitting unit for transmission on the patient's body via body coupled communication;
   a transceiver that receives at least the beacon or patient identification information from the transmitting unit via body coupled communication when the transceiver is touching or in close proximity with the patient and forwards at least the beacon or patent identification information to a hospital system including an interface for receiving information from the transceiver wirelessly or by a wired connection and storing it in a medical facility database; and
   a body coupled communication device connected with an appliance or a caregiver which, when the caregiver or appliance is touching or in close proximity to the patient, transmits an appliance key to the receiving unit, receives the beacon or patient identification information encrypted with the appliance key from the transmitting unit, and communicates an identification of the appliance or caregiver to the receiving unit, the identification of the appliance or caregiver being encrypted with the appliance key.

2. The system according to claim 1, wherein the beacon identification information is different from a patient ID and wherein the interface correlates information received from the transceiver with a patient associated with the beacon identification information.

3. The system according to claim 2, wherein the transceiver receives encrypted patient data from a diagnostic or test apparatus, associates the encrypted patient data and the beacon identification information, and transmits the encrypted patient data and the beacon identification information to the hospital system wirelessly or by a wired connection, and the interface correlates beacon identification information with a patient ID.

4. The system according to claim 1, further including:
   a body coupled communication device connected with an appliance or a caregiver which, when the caregiver or appliance is touching or in close proximity to the patient, performs at least one of receiving the beacon identification from the transmitting unit and communicating an identification of the appliance or caregiver to the transmitting unit.

5. The system according to claim 1, wherein the flexible circuit includes a receiving unit that receives body coupled communications that:
   (i) request transmission of the beacon identification information;
   (ii) convey a caregiver identification from a treating caregiver; and
   (iii) convey monitored physiological, administered medication, or clinical lab data,
   wherein the receiving unit is connected with the memory to store the caregiver information and the monitored physiological, administered medication or clinical lab data.

6. The system according to claim 1, wherein
   the memory is configured to store an encryption key,
   the wireless transmitting unit is configured to transmit the encryption key via the body coupled communication protocol to physiological sensors mounted in body coupled communication contact with the patient, and the receiving unit is configured to receive encrypted physiological data from the physiological sensors via the body coupled communication protocol.

7. The system according to claim 1, further including:
   a body coupled communication device connected with an appliance or a caregiver which, when the caregiver or appliance is touching or in close the patient, communicates an identification of the appliance or caregiver to a receiving unit of the flexible circuit which stores the identification of the appliance or caregiver in the memory of the flexible circuit.

8. The system according to claim 7, wherein the flexible circuit transmits the stored identification of the appliance or caregiver when the wireless transmitting unit is in bodied coupled communication with the transceiver, the transceiver transmitting the identification of the appliance or caregiver to the medical database.

9. The beacon system of claim 1, wherein the processor encrypts the beacon identification and communicates the encrypted beacon identification to the transceiver in response to the transceiver issuing a request to the processor via body coupled communication.

10. A hospital system comprising:
  a plurality of beacon apparatuses for attachment to a plurality of patients; each beacon apparatus comprising:
    a strap of flexible material configured to be attached to an extremity of a patient;
    a printable layer attached to the strap;
    a flexible power supply attached to the strap; and,
    a flexible circuit attached to the strap and the power supply, the flexible circuit including:
      a wireless transmitting unit which wirelessly transmits at least beacon identification information;
      a memory that stores at least the beacon identification information and an encryption key; and,
      a processor that at least encrypts the beacon identification information with the encryption key and communicates the encrypted beacon identification information from the memory to the transmitting unit for transmission on the patient's body via the body coupled communications;
  a transceiver for receiving the encrypted beacon identification information from the beacon apparatuses and transmitting information to the beacon apparatuses;
  a medical facility system connected wirelessly or by a wired connection with the transceiver for storing and retrieving patient information, the medical facility system including an interface which decrypts the encrypted beacon identification information and correlates received beacon identification information to a patient associated with the beacon identification information;
  a diagnostic or testing apparatus for receiving encrypted beacon identification information from the transceiver and providing encrypted diagnostic or test information and the associated encrypted beacon identification information received from the transceiver to the medical facility system; and,
  a display and user input device connected with the transceiver.

11. The system according to claim 10, wherein the diagnostic or testing apparatus electronically associates the beacon identification information with the diagnostic or test results, communicates the beacon identification information and the diagnostic or test results to the transceiver which transmits the associated beacon identification information and diagnostic or test results to the interface of the medical facility system.

12. The hospital system of claim 10, wherein the diagnostic or testing apparatus includes an IV pump which receives the encrypted beacon identification information from the transceiver and provides encrypted diagnostic information including medical dosage information to the medical facility system.

13. The hospital system of claim 10, wherein the diagnostic or testing apparatus includes a blood pressure monitor which receives the encrypted beacon identification information from the transceiver and provides encrypted diagnostic information including blood pressure and pulse rate information to the medical facility system.

14. A method of associating information with a patient, the method comprising:
  printing human readable patient information on a printable layer;
  attaching together the printable layer, a strap of flexible material, a flexible circuit layer including a body coupled communication transceiver, a memory, and a processor, and a flexible power supply;
  attaching the flexible strip with the attached printable layer, flexible circuit layer, and flexible power supply to an extremity of the patient;
  bringing the patient into body coupled communication contact with a transceiver and via the body coupled communications contact loading the memory with a patient identification information, a medical history of the patient, and encryption key via a body coupled communication protocol;
  bringing the patient into body coupled contact with a transceiver associated with a diagnostic, monitoring, therapy, or testing apparatus to at least one of transfer the patient identification information from the flexible circuit layer memory to the diagnostic, monitoring, therapy, or testing apparatus or transfer information from the diagnostic, monitoring, therapy, or testing apparatus to the flexible circuit layer memory;
  performing a diagnostic, monitoring, therapy, or testing operation with a diagnostic, monitoring, therapy, or testing apparatus to generate diagnostic, monitoring, therapy, or test results;
  encrypting the diagnostic, monitoring, therapy, or test results with the encryption key and electronically associating the patient identification information with the encrypted diagnostic, monitoring, therapy, or test results; and
  transmitting at least the patient identification information and the encrypted diagnostic, monitoring, therapy, or test results in a wired or wireless communication protocol, on a wired or wireless communication network which carries the patient identifier and the encrypted diagnostic monitoring, therapy, or test results to a medical database.

15. The method of claim 14, further including:
  bringing a caregiver equipped with a caregiver body coupled communication device into body coupled communication contact with the patient, the body coupled communication device including a caregiver identification;
  communicating the caregiver identification information from the caregiver body coupled communication device via body coupled communications to the flexible circuit layer memory to store a record of interaction with the caregiver including the caregiver identification information; and
  transmitting the caregiver identification information with at least the patient identification information to the medical database via the wireless or wired communication network.

* * * * *